US008282563B2

(12) United States Patent
Uemura et al.

(10) Patent No.: US 8,282,563 B2
(45) Date of Patent: Oct. 9, 2012

(54) CARDIAC DISEASE TREATMENT SYSTEM

(75) Inventors: Kazunori Uemura, Toyonaka (JP);
Atsunori Kamiya, Suita (JP); Masaru Sugimachi, Suita (JP); Kenji Sunagawa, Fukuoka (JP)

(73) Assignee: Japan Health Sciences Foundation, Tokyo (JP)

( * ) Notice: Subject to any disclaimer, the term of this patent is extended or adjusted under 35 U.S.C. 154(b) by 847 days.

(21) Appl. No.: 11/719,400

(22) PCT Filed: Nov. 18, 2004

(86) PCT No.: PCT/JP2004/017154
§ 371 (c)(1),
(2), (4) Date: Mar. 9, 2009

(87) PCT Pub. No.: WO2006/054343
PCT Pub. Date: May 26, 2006

(65) Prior Publication Data
US 2009/0221923 A1 Sep. 3, 2009

(51) Int. Cl.
*A61B 5/02* (2006.01)
(52) U.S. Cl. .............. 600/485; 604/65; 604/66; 604/67; 604/31; 604/503
(58) Field of Classification Search .................. 600/526, 600/481–507, 300–301; 604/890.1, 891.1, 604/31, 65–67, 503, 505
See application file for complete search history.

(56) References Cited

U.S. PATENT DOCUMENTS 4,269,193 A * 5/1981 Eckerle ........................ 600/485
5,289,823 A * 3/1994 Eckerle ........................ 600/492
6,090,047 A * 7/2000 Kass et al. .................... 600/485
6,292,689 B1 * 9/2001 Wallace et al. ............... 600/547
6,527,698 B1 * 3/2003 Kung et al. .................... 600/16
(Continued)

FOREIGN PATENT DOCUMENTS
JP 1305962 12/1989
(Continued)

OTHER PUBLICATIONS ("Carotid Sinus Baroreceptor Reflex Control and Epinephrine: Influence on Capacitive and Resistive Properties of the Total Pulmonary Vascular Bed of the Dog" Shoukas Artin. Circ. Res. 51:95-101, 1982.*

(Continued)

*Primary Examiner* — Navin Natnithithadha
*Assistant Examiner* — Sunita Reddy
(74) *Attorney, Agent, or Firm* — Mark M Friedman

(57) ABSTRACT

Problems
To provide a cardiac disease treatment system for accurately diagnosing the functional cause of an abnormality of a cardiac disease by analyzing the hemodynamic state of a patient, automatically performing medication in accordance with the diagnosis result, and treating the cardiac disease.
Means for solving problems
The cardiac disease treatment system is characterized by comprising input means (2) for inputting the cardiac output value of the patient, the left atrial pressure value and/or the right atrial pressure value, first calculating means (31) for calculating the pumping ability value of the left heart or the right heart from the inputted cardiac output and the left or right atrial pressure value, first comparing means (41) for comparing the pumping ability value of the left heart or the right heart with a target pumping ability value, and first medicating means (51) for medicating the patient in accordance with the result of the comparison by the first comparing means (41).

25 Claims, 7 Drawing Sheets

U.S. PATENT DOCUMENTS

| | | | |
|---|---|---|---|
| 6,540,658 B1* | 4/2003 | Fasciano et al. | 600/17 |
| 7,666,144 B2* | 2/2010 | Cohen et al. | 600/485 |
| 2001/0025137 A1* | 9/2001 | Webb et al. | 600/300 |
| 2002/0038090 A1* | 3/2002 | Sunagawa et al. | 600/485 |
| 2002/0161304 A1* | 10/2002 | Eide | 600/485 |
| 2003/0195409 A1* | 10/2003 | Seitz et al. | 600/407 |
| 2003/0199779 A1* | 10/2003 | Muhlenberg et al. | 600/513 |
| 2004/0019285 A1* | 1/2004 | Eigler et al. | 600/488 |
| 2004/0064086 A1* | 4/2004 | Gottlieb et al. | 604/43 |
| 2004/0106874 A1* | 6/2004 | Eigler et al. | 600/486 |
| 2004/0254480 A1* | 12/2004 | Band et al. | 600/482 |
| 2004/0267086 A1* | 12/2004 | Anstadt et al. | 600/17 |
| 2005/0090753 A1* | 4/2005 | Goor et al. | 600/508 |
| 2005/0124903 A1* | 6/2005 | Roteliuk et al. | 600/526 |
| 2005/0124904 A1* | 6/2005 | Roteliuk | 600/526 |

FOREIGN PATENT DOCUMENTS

| | | |
|---|---|---|
| JP | 2000507129 | 6/2000 |
| WO | WO97/34648 | 9/1997 |
| WO | WO2006/054343 | 5/2006 |

OTHER PUBLICATIONS

Arthur C. Guyton *Determination of Cardiac Output by Equating Venous Return Curves with Cardiac Response Curves* pp. 123-129 From the Dept of Physiology and Biophysics School of Medicine University of Mississippi.

Artin A. Shoukas: "Carotid Sinus Baroreceptor Reflex Control and Epinephrine. Influence on Capacitive and Resistive Properties of the Total Pulmonary Vascular Bed of the Dog", Circ Res 51 pp. 95-101, 1982.

* cited by examiner

CARDIAC DISEASE TREATMENT SYSTEM

CROSS-REFERENCE TO RELATED APPLICATION

This is a national phase of International Patent Application No. PCT/JP2004/017154, with an international filing date of Nov. 18, 2004.

BACKGROUND OF THE INVENTION

Field of the Invention

The present invention relates to a cardiac disease treatment system. More specifically, the present invention relates to a system for treating cardiac diseases by accurately diagnosing the causes of abnormalities of cardiac diseases and then automatically administering drugs in response to the result of diagnosis.

Emergency care provided by specialized cardiologists is known to be very effective for cardiac diseases in the acute phase. However, only 3% of all physicians are specialists who are capable of treating cardiac diseases, and they are by no means adequate to provide care for all the cardiac disease patients.

Thus, there is a need for general physicians to acquire a level of competence comparable to cardiology specialists to treat cardiac diseases.

However, it is very difficult for general physicians to attain a level of competence comparable to cardiology specialists. Therefore, development of a cardiac disease treatment system that provides general physicians with therapeutic skills comparable to those of cardiology specialists has become a necessity.

As a treatment system intended to solve the said problems, a system that automatically adjusts the intravenous administration of cardiovascular drugs has been created, as disclosed in Tokuhyou 2000-507129. The system disclosed in Tokuhyou 2000-507129 automatically regulates the intravenous administration of cardiovascular drugs such as vasodilators to a patient aiming to stabilize the drug concentrations in blood during anesthesia and other clinical conditions.

The system described in Tokuhyou 2000-507129, however, aims at controlling the drug concentration in blood or the pharmacokinetics of the drug in the patient's body, and does not aim at improving the hemodynamic parameters or the organ systems of the patient. Also, the system is intended to be used only in patients under anesthesia, and therefore does not solve the said problem.

On the other hand, the basic circulatory equilibrium theory utilizing cardiac output curve and venous return curve was established by Guyton et al. in the 1950's, and studies that attempt to apply this circulatory equilibrium theory to the treatment of cardiac diseases have been conducted (see "Determination of cardiac output by equating venous return curves with cardiac response curves" Physiol Rev 35:123-129, 1955).

However, Guyton's basic circulatory equilibrium theory does not take into account redistribution of blood between the pulmonary and systemic circulations, and does not allow prediction of left atrial pressure (pulmonary arterial wedge pressure) that impacts the prognosis. Thus, there is an issue of not able to conduct accurate treatment.

Many existing devices are capable of measuring cardiac output, left atrial pressure, arterial blood pressure, and heart rate, as well as indicating abnormalities in hemodynamics. However, even though the values of hemodynamic abnormalities are displayed, none of the devices developed hitherto are capable of determining whether the hemodynamic abnormalities are attributed to the cardiac pumping capability or to the effective circulating blood volume, i.e., making an inner working diagnosis of the circulatory system.

As described above, even though hemodynamic abnormalities are measured, the component in the circulatory system causing these abnormalities cannot be diagnosed. Consequently the decision of treatment method depends entirely on the experience of said cardiology specialists.

SUMMARY OF THE INVENTION

Considering the above-mentioned problems, the present invention relates to a cardiac disease treatment system that treats cardiac disease by accurately diagnosing the causes of abnormalities of cardiac diseases through analyzing the patient's hemodynamics and automatically administering drugs appropriate to the diagnosis.

In order to achieve the above object, the present invention provides a cardiac disease treatment system comprising:

an input means inputting a cardiac output value, a left atrial pressure value, and a right atrial pressure value of a patient;

a first calculation means calculating a pumping ability value of the left heart or a pumping ability value of the right heart from the cardiac output value, the left atrial pressure value, and the right atrial pressure value which are input from the input means;

a first comparison means comparing calculated values of the pumping ability value of the left heart and—the pumping ability value of the right heart and target pumping ability values; and a first dosing means administering drugs to the patient according to comparison results in the first comparison means.

The present invention may provide the cardiac disease treatment system, wherein the first calculation means uses equation 1 and equation 2 to calculate the pumping ability value of the left heart and the pumping ability value of the right heart from the cardiac output value, the left atrial pressure value, and the right atrial pressure value input by the input means;

$$\text{(cardiac output value)} = \text{(left cardiac pumping capability value)} \times \{\text{Log}((\text{left atrial pressure value}) - A) + B\} \quad \text{Equation 1}$$

(where A and B are constants)

$$\text{(cardiac output value)} = \text{(right cardiac pumping capability value)} \times \{\text{Log}((\text{right atrial pressure value}) - C) + D\} \quad \text{Equation 2}$$

(where C and D are constants)

The present invention may provide the cardiac disease treatment system, further comprising:

a first target decision means calculating a target pumping ability value of the left heart and a target pumping ability value of the right heart as the target pumping ability value from the target cardiac output value, the target left atrial pressure value, and the target right atrial pressure value.

The present invention may provide the cardiac disease treatment system, wherein the first target decision means uses equation 3 and equation 4 to calculate the target pumping ability value of the left heart and the pumping ability value of the right heart from the target cardiac output value, the target left atrial pressure value, and the right atrial pressure value:

$$\text{(target left cardiac pumping capability value)} = \text{(target cardiac output value)} / \{\text{Log}((\text{target left atrial pressure value}) - A) + B\} \quad \text{Equation 3}$$

(where A and B are constants)

$$\text{(target right cardiac pumping capability value)} = \text{(target cardiac output value)} / \{\text{Log}((\text{target right atrial pressure value}) - C) + D\} \qquad \text{Equation 4}$$

(where C and D are constants)

In order to achieve the above object, the present invention provides a cardiac disease treatment system comprising:

an input means inputting a cardiac output value, a left atrial pressure value, and a right atrial pressure value of a patient;

a second calculation means calculating an effective circulating blood volume value from the cardiac output value, the left atrial pressure value, and the right atrial pressure value which are input from the input means;

a second comparison means comparing the effective circulating blood volume value calculated by the second calculation means and a target effective circulating blood volume value; and a second dosing means administering drugs to the patient according to the comparison result in the second comparison means.

The present invention may provide the cardiac disease treatment system, wherein the second comparison means uses equation 5 to calculate the effective circulating blood volume value from the cardiac output value, the left atrial pressure value, and the right atrial pressure value input by the input means;

$$\text{(cardiac output value)} = \frac{1}{E}(\text{effective circulating blood volume value}) - F(\text{right atrial pressure value}) - G(\text{left atrial pressure value}) \qquad \text{Equation 5}$$

(where E, F, and G are constants)

The present invention may provide the cardiac disease treatment system, further comprising:

a second target decision means calculating a target effective circulating blood volume value from the target cardiac output value, the target left atrial pressure value, and the target right atrial pressure value.

The present invention may provide the cardiac disease treatment system, wherein the second target decision means uses equation 6 to calculate the target effective circulating blood volume value from the target cardiac output value, the target left atrial pressure value, and the target right atrial pressure value:

$$\text{(target effective circulating blood volume value)} = \{(\text{target cardiac output value}) + F(\text{target right atrial pressure value}) + G(\text{target left atrial pressure value})\} \times E \qquad \text{Equation 6}$$

(where E, F, and G are constants)

In order to achieve the above object, the present invention provides a cardiac disease treatment system comprising:

an input means inputting a cardiac output value, a right atrial pressure value, and an arterial blood pressure value of a patient;

a third calculation means calculating a vascular resistance value from the cardiac output value, the right atrial pressure value, and the arterial blood pressure value which are input by the input means;

a third comparison means comparing the vascular resistance value calculated by the third calculation means and a target vascular resistance value; and a third dosing means administering drugs to the patient according to the comparison result in the third comparison means.

The present invention may provide the cardiac disease treatment system, wherein the third comparison means uses equation 7 to calculate the vascular resistance value from the cardiac output value, the right atrial pressure value, and the arterial blood pressure value input by the input means:

$$\text{(vascular resistance value)} = \{(\text{arterial blood pressure value}) - (\text{right atrial pressure value}) - H\} / (\text{cardiac output value}) \qquad \text{Equation 7}$$

(where H is a constant)

The present invention may provide the cardiac disease treatment system, further comprising:

a third target decision means calculating a target vascular resistance value from the target cardiac output value, the target arterial blood pressure value, and the target right atrial pressure value.

The present invention may provide the cardiac disease treatment system, wherein the third target decision means uses equation 8 to calculate the target vascular resistance value from the target cardiac output value, the target arterial blood pressure value, and the target right atrial pressure value:

$$\text{(target vascular resistance value)} = \{(\text{target arterial blood pressure value}) - (\text{target right atrial pressure value}) - H\} / (\text{target cardiac output value}) \qquad \text{Equation 8}$$

(where H is a constant)

In order to achieve the above object, the present invention provides a cardiac disease treatment system that is a combination of two or three of the systems defined in following (i) to (iii).

(i) A cardiac disease treatment system comprising:

an input means inputting a cardiac output value, a left atrial pressure value, and a right atrial pressure value of a patient;

a first calculation means calculating a pumping ability value of the left heart or a pumping ability value of the right heart from the cardiac output value, the left atrial pressure value, and the right atrial pressure value which are input from the input means;

a first comparison means comparing calculated values of the pumping ability value of the left heart and the pumping ability value of the right heart and target pumping ability values; and a first dosing means administering drugs to the patient according to comparison results in the first comparison means.

(ii) A cardiac disease treatment system comprising:

an input means inputting a cardiac output value, a left atrial pressure value, and a right atrial pressure value of a patient;

a second calculation means calculating an effective circulating blood volume value from the cardiac output value, the left atrial pressure value, and the right atrial pressure value which are input from the input means;

a second comparison means comparing the effective circulating blood volume value calculated by the second calculation means and a target effective circulating blood volume value; and a second dosing means administering drugs to the patient according to the comparison result in the second comparison means.

(iii) A cardiac disease treatment system comprising:

an input means inputting a cardiac output value, a right atrial pressure value, and an arterial blood pressure value of a patient;

a third calculation means calculating a vascular resistance value from the cardiac output value, the right atrial pressure value, and the arterial blood pressure value which are input by the input means;

a third comparison means comparing the vascular resistance value calculated by the third calculation means and a target vascular resistance value; and a third dosing means administering drugs to the patient according to the comparison result in the third comparison means.

The present invention may provide the cardiac disease treatment system, further comprising:

a display means continuously displaying each of the calculated values calculated by the calculation means in chronological order.

The present invention may provide the cardiac disease treatment system, wherein the cardiac output value is measured by a Swan-Ganz catheter or calculated from a diastolic time constant of arterial blood pressure waveform.

The present invention may provide the cardiac disease treatment system, wherein the left atrial pressure value is directly measured by a catheter or continuously estimated from diastolic pressure values of pulmonary capillary wedge pressure or pulmonary arterial pressure which are measured by a Swan-Ganz catheter.

By providing the above inventions, the said issues will be resolved.

The invention defined in Claim 1 provides a cardiac disease treatment system that has the capability to diagnose abnormality of cardiac pumping capability by inputting a patient's cardiac output, left atrial pressure and right atrial pressure values and calculating the left cardiac pumping capability and right cardiac pumping capability, followed by comparing the calculated left cardiac pumping capability and right cardiac pumping capability with target cardiac pumping capability values; and to administer drugs in response to the result of diagnosis.

Because drugs are administered according to the result of comparison between left/right cardiac pumping capability values and target cardiac pumping capability values, treatment can reliably and accurately alter the abnormal state of a patient's cardiac pumping capability to a normal state.

The invention defined in Claim 2 provides a cardiac disease treatment system that not only enables more detailed and precise calculation of cardiac pumping capability by Equations 1 and 2, but by appropriately varying Constants A to D, also allows correction of cardiac pumping capability values calculated from patients with diverse diseases.

Correction of the calculated cardiac pumping capability in individual patient allows more accurate calculation of cardiac pumping capability and more precise treatment for each patient.

The invention defined in Claim 3 provides a cardiac disease treatment system that allows easy calculation of target cardiac pumping capability (target left cardiac pumping capability and right cardiac pumping capability) values using target cardiac output, target left atrial pressure and target right atrial pressure values.

The invention defined in Claim 4 provides a cardiac disease treatment system that can calculate the target cardiac pumping capability value more appropriately by using Equations 3 and 4.

The invention defined in Claim 5 provides a cardiac disease treatment system capable of calculating the patient's effective circulating blood volume from patient's input data of cardiac output, left atrial pressure, and right atrial pressure; comparing the calculated effective circulating blood volume value with a target effective circulating blood volume value; and administering drugs in response to the result of comparison.

Because drugs are administered according to the result of comparison between, the calculated effective circulating blood volume and target effective circulating blood volume, treatment can reliably and accurately alter the abnormal state of a patient's effective circulating blood volume to a normal state.

The invention defined in Claim 6 provides a cardiac disease treatment system that not only enables more detailed and precise calculation of effective circulating blood volume by Equation 5, but by appropriately varying Constants E to G, also allows correction of effective circulating blood volume values calculated from patients with diverse diseases.

Correction of the calculated effective circulating blood volume in individual patient allows more accurate calculation of effective circulating blood volume and more precise treatment for each patient.

The invention defined in Claim 7 provides a cardiac disease treatment system that allows easy calculation of target effective circulating blood volume from the target cardiac output, target left atrial pressure, and target right atrial pressure values.

The invention defined in Claim 8 provides a cardiac disease treatment system that can calculate the target effective circulating blood volume more appropriately by using Equation 6.

The invention defined in Claim 9 provides a cardiac disease treatment system capable of calculating a patient's vascular resistance from patient's input data of cardiac output, right atrial pressure, and arterial blood pressure; comparing the calculated vascular resistance value with the target vascular resistance value; and administering drugs in response to the result of comparison.

Because drugs are administered according to the result of comparison between the calculated vascular resistance value and target vascular resistance value, treatment can reliably and accurately alter the abnormal state of a patient's vascular resistance to a normal state.

The invention defined in Claim 10 provides a cardiac disease treatment system that enables more detailed and precise calculation of vascular resistance by using Equation 7. Constant H of Equation 7 is a constant that corrects for nonlinearity of vascular resistance. Thus by adjusting this constant, the system can be operated normally even in individuals showing strong nonlinearity.

The invention defined in Claim 11 provides a cardiac disease treatment system that allows easy calculation of target vascular resistance value from the target cardiac output, target right atrial pressure, and target arterial blood pressure values.

The invention defined in Claim 12 provides a cardiac disease treatment system that can calculate the target vascular resistance value more appropriately by using Equation 8.

The invention defined in Claim 13 provides a cardiac disease treatment system capable of calculating the patient's left cardiac pumping capability and right cardiac pumping capability, effective circulating blood volume, and vascular resistance values from patient's cardiac output, right atrial pressure and left atrial pressure, and arterial blood pressure; comparing these calculated values with the target values; and administering drugs in response to the results of these comparisons.

This enables effective drug administrations to alter a patient's abnormal states of left cardiac pumping capability and right cardiac pumping capability, effective circulating blood volume, and vascular resistance to the respective normal states.

The invention defined in Claims 14 to 17 provides a cardiac disease treatment system that can chronologically display the respective values of left cardiac pumping capability and right cardiac pumping capability, effective circulating blood volume, and vascular resistance, thus preventing overlooking of chronological changes and ensuring a reliable diagnosis of the patient, and meanwhile can also display the changes in patient's conditions as a result of drug administration.

The invention defined in Claims 18 to 25 provides a highly accurate cardiac disease treatment system because cardiac output is measured by a Swan-Ganz catheter or calculated from a diastolic time constant of arterial blood pressure waveform, while left atrial pressure is directly measured by a catheter or continuously estimated from the diastolic value of pulmonary capillary wedge pressure or pulmonary arterial pressure measured by a Swan-Ganz catheter.

DETAILED DESCRIPTION

Figure 1:
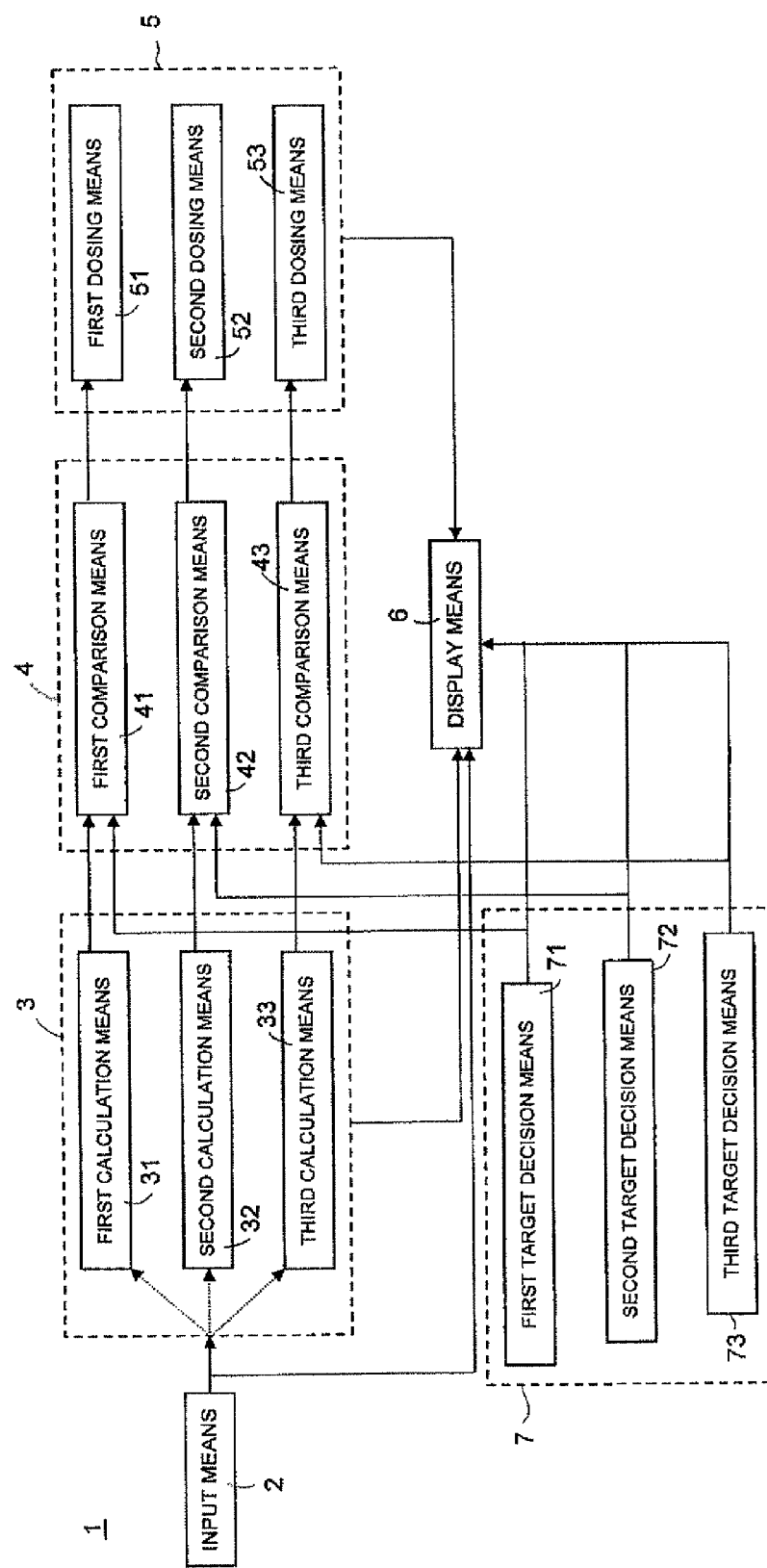
FIG. 1 is a schematic block diagram of the cardiac disease treatment system relating to the present invention.
Figure 2:
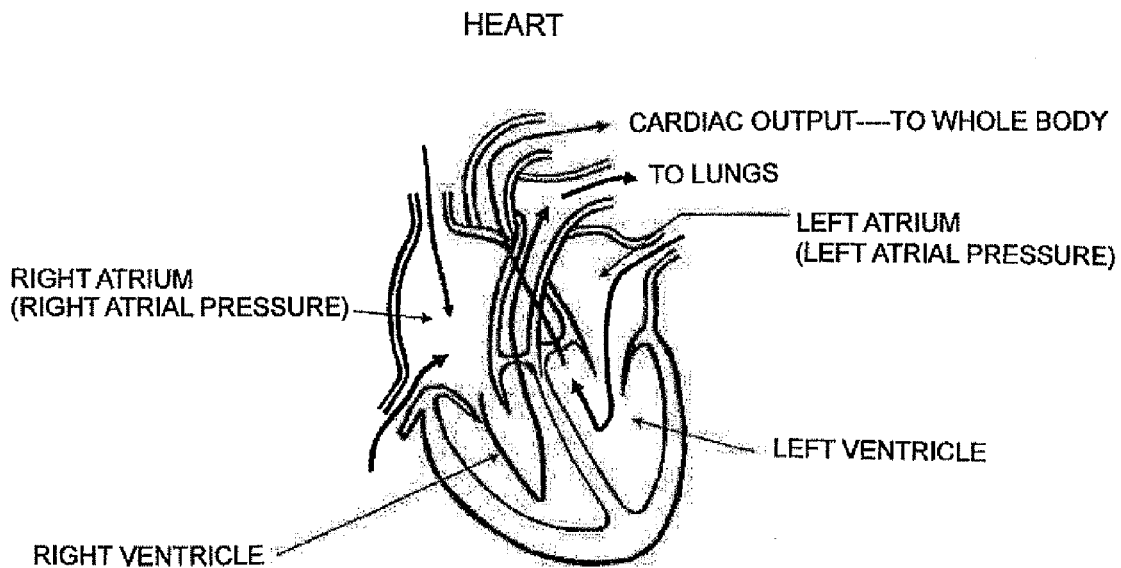
FIG. 2 is a schematic drawing of a heart.

FIG. 1 is a schematic block diagram showing the cardiac disease treatment system relating to the present invention. FIG. 2 is a schematic view of a heart. Cardiac Disease Treatment System (1) relating to the present invention utilizes cardiac output (CO), left atrial pressure (Pla), and right atrial pressure (Pra) (shown in FIG. 2), as well as arterial blood pressure (AP) (not shown in FIG. 2).

Using Cardiac Disease Treatment system (1) relating to the present invention, it is possible to diagnose whether abnormality exists within each of the components of the cardiovascular system based on hemodynamic abnormalities [reduction in CO (peripheral circulatory failure), elevation in Pla (pulmonary congestion), and increase or decrease in arterial blood pressure], and to administer appropriate therapeutic agents.

Cardiac Disease Treatment System (1) includes Input Means (2), Calculation Means (3), Comparison Means (4), Drug Administration Means (5), Display Means (6), and Target Decision Means (7).

Input Means (2) inputs hemodynamic values (numerical data) measured from a patient into Calculation Means (3) (to be described below). Input Means (2) is configured to input hemodynamic values of AP, CO, Pra, and Pla.

The configuration of Input Means (2) is not specified, as long as numerical data can be input into Calculation Means (3). It may be an input device such as a keyboard used by the user of Cardiac Disease Treatment System (1) to input actually measured values, or a measuring device that measures the patient's hemodynamics and inputs the values directly into Calculation Means (3). If Cardiac Disease Treatment System (1) is constantly connected to a patient for diagnosis of cardiac disease and drug administration, then a configuration of measuring the patient's hemodynamics and direct inputting into Calculation Means (3) is preferred.

The numerical data of hemodynamics input by Input Means (2) are AP, CO, Pra, and Pla, and each can be measured by a conventional measuring device. The measuring devices are not specified. A catheter placed in a peripheral artery (such as radial artery) can be used to measure AP, and a Swan-Ganz catheter can be used to measure CO, Pla, and Pra.

In order to perform continuous diagnosis in a patient, Cardiac Disease Treatment System (1) relating to the present invention uses continuous numerical data for each parameter. However, while AP and Pra can be measured continuously, continuous measurements of Pla and CO are considered impossible.

Therefore, continuous data of Pla are obtained using the method of continuously estimating Pla from pulmonary artery diastolic pressure.

Because Pla is known to show a linear relationship with pulmonary artery diastolic pressure, Pla may be calculated from pulmonary artery diastolic pressure based on the mean correlation obtained from multiple individuals. When calculating Pla from pulmonary artery diastolic pressure, because the correlation (linear relationship) between pulmonary artery diastolic pressure and Pla changes depending on heart rate, it is preferable to correct for heart rate when determining the mean correlation from multiple individuals.

Continuous data of CO are obtained using the method of estimating CO from the diastolic time constant of peripheral blood pressure waveform.

CO may be obtained from conventional methods, such as calculation from the diastolic time constant of peripheral blood pressure waveform.

Target Decision Means (7) allows easy calculations of target values [target cardiac pumping capability (target left cardiac pumping capability and target right cardiac pumping capability), target effective circulating blood volume, and target vascular resistance] that are used as reference values in First to Third Comparison Means (to be described below). These target values [target cardiac pumping capability (target left cardiac pumping capability and target right cardiac pumping capability), target effective circulating blood volume, and target vascular resistance] may be input directly by the user into the corresponding comparison means. Alternatively, by using Target Decision Means (7), target cardiac pumping capability (target left cardiac pumping capability and target right cardiac pumping capability), target effective circulating blood volume, and target vascular resistance values are calculated automatically by just inputting target CO, target Pla, target Pra, and target AP.

Target Decision Means (7) is composed of First Target Decision Means (71), Second Target Decision Means (72), and Third Target Decision Means (73). First to Third Target Decision Means (71-73) are processing units configured to calculate output values according to input values.

Target Decision Means (7) may be a single processing unit configured to perform all computations for First to Third Target Decision Means (71-73). Alternatively, Target Decision Means (7) may be composed of three processing units that perform computations for each of the First to Third Target Decision Means (71-73).

First target decision means (71) calculates the target left cardiac pumping capability from target CO and target Pla values, and calculates target right cardiac pumping capability from the target CO and target Pra values.

First Target Decision Means (71) may be configured to calculate both the target left cardiac pumping capability and target right cardiac pumping capability, or to calculate either the target left cardiac pumping capability or target right cardiac pumping capability.

Regarding the method of calculating target left cardiac pumping capability by First Target Decision Means (71), the target CO and target Pla values are substituted into Equation 9 shown below to compute the target left cardiac pumping capability value.

Constants A and B in Equation 9 are constants that can be varied appropriately according to individual patient. These constants are predetermined by the user and can be varied according to patient. Thus adjustment in individual patient allows correction of the target left cardiac pumping capability.

$$(\text{target left cardiac pumping capability}) = (\text{target CO}) / \{Log((\text{target Pla}) - A) + B\} \quad \text{Equation 9}$$

(where A and B are constants)

Besides calculating target left cardiac pumping capability as described above, First Target Decision Means (71) can similarly calculate target right cardiac pumping capability value using Equation 10 shown below. Target right cardiac pumping capability is calculated by substituting the target CO and target Pra values into Equation 10.

Constants C and D in Equation 10 are constants that can be varied appropriately according to individual patient. These constants are predetermined by the user and can be varied according to patient. Thus adjustment in individual patient allows correction of the target right cardiac pumping capability.

$$(\text{target right cardiac pumping capability}) = (\text{target CO}) / \{Log((\text{Target Pra}) - C) + D\} \quad \text{Equation 10}$$

(where C and D are constants)

Target Decision Means (7) comprises Second Target Decision Means (72), as described above.

Second Target Decision Means (72) calculates target effective circulating blood volume from the target CO, target Pla, and target Pra values.

Regarding the method of calculating target effective circulating blood volume by Second Target Decision Means (72), the target CO, target Pla, and target Pra values are substituted into Equation 11 shown below to compute the target effective circulating blood volume value.

Constants E, F, and G in Equation 11 are constants that can be varied appropriately according to individual patient. These constants are predetermined by the user and can be varied according to patient. Thus adjustment in individual patient allows correction of the calculated effective circulating blood volume.

$$(\text{target effective circulating blood volume}) = \{(\text{target CO}) + F(\text{target Pra}) + G(\text{Target Pla})\} \times E \quad \text{Equation 11}$$

(where E, F, and G are constants)

Target Decision Means (7) comprises Third Target Decision Means (73), as described above.

Third. Target Decision Means (73) calculates target vascular resistance value from the target CO, target Pra, and target AP values.

Regarding the method of calculating target vascular resistance by Third Target Decision Means (73), the target CO, target Pra, and target AP values are substituted into Equation 12 shown below to compute the target vascular resistance value. Constant H in Equation 12 is a constant that corrects for non-linearity of vascular resistance. Thus by adjusting this constant in individual patient, the system can be operated normally even in individuals showing strong nonlinearity.

$$(\text{target vascular resistance}) = \{(\text{target AP}) - (\text{target Pra}) - H)\} / (\text{target CO}) \quad \text{Equation 12}$$

(where H is a constant)

The above-mentioned target values (CO, Pla, Pra, and AP) are values input into Target Decision Means (7) by the user. The user inputs these values to obtain the desired patient conditions.

Calculation Means (3) carries out computation by predetermined methods using the hemodynamic values input from Input Means (2). Calculation Means (3) is composed of First Calculation Means (31), Second Calculation Means (32), and Third Calculation Means (33). Calculation Means (3) may be a single processing unit configured to perform all calculations of First to Third Calculation Means (31-33). Alternatively, Calculation Means (3) may be composed of three processing units that separately perform calculations of First to Third Calculation Means (31-33).

First Calculation Means (31) calculates left cardiac pumping capability from the CO and Pla values input from Input Means (2). Alternatively, First Calculation Means (31) calculates right cardiac pumping capability from the CO and Pra values input from Input Means (2). First Calculation Means (31) may be configured to calculate both left cardiac pumping capability and right cardiac pumping capability, or to calculate either left cardiac pumping capability or right cardiac pumping capability.

Regarding the method of calculating left cardiac pumping capability by First Calculation Means (31), the CO and Pla values input from Input Means (2) are substituted into Equation 13 shown below to compute left cardiac pumping capability.

Constants A and B in Equation 13 are constants that can be varied appropriately according to individual patient. These constants are predetermined by the user and can be varied according to patient. Thus adjustment in individual patient allows correction of the calculated left cardiac pumping capability.

$$(CO) = (\text{left cardiac pumping capability}) \times \{Log((Pla) - A) + B\} \quad \text{Equation 13}$$

(where A and B are constants)

In using the above equation, it is preferable to convert the equation to Equation 14 as shown below, and to configure such that left cardiac pumping capability is calculated from the input data from Input Means (2). Use of the converted equation allows fast arithmetic processing.

$$(\text{left cardiac pumping capability}) = (CO) / \{Log((Pla) - A) + B\} \quad \text{Equation 14}$$

(where A and B are constants)

Besides calculating left cardiac pumping capability as described above, First Calculation Means (31) can similarly calculate right cardiac pumping capability using Equation 15 as shown below. Right cardiac pumping capability is calculated by substituting the CO and Pra values into Equation 15.

In this case also, it is preferable to convert Equation 15 to Equation 16 as shown below, and to configure First Calculation Means (31) such that right cardiac pumping capability is calculated from the input values from Input Means (2).

Constants C and D in Equations 15 and 16 are constants that can be varied appropriately according to individual patient. These constants are predetermined by the user and can be varied according to patient. Thus adjustment in individual patient allows correction of the calculated right cardiac pumping capability.

$$(CO) = (\text{right cardiac pumping capability}) \times \{\text{Log}((\text{Pra})-C)+D\} \quad \text{Equation 15}$$

(where C and D are constants)

$$(\text{right cardiac pumping capability}) = (CO)/\{\text{Log}((\text{Pra})-C)+D\} \quad \text{Equation 16}$$

(where both C and D are constants)

First calculation means (31) calculates left cardiac pumping capability and right cardiac pumping capability, and either cardiac pumping capability can be calculated using the CO value. Thus it is possible to show their relationship by plotting "CO" values, "Pla" values, and "Pra" values on the three axes of a three-dimensional coordinate, as shown in FIG. 3.

By plotting "CO" values, "Pla" values, and "Pra" values on the three axes of a three dimensional coordinate, a CO curve can be drawn that represents the change in CO. The CO curve allows visualization of the integrated cardiac pumping capability of the patient's left and right heart, which greatly facilitates diagnosis.

Figure 3:
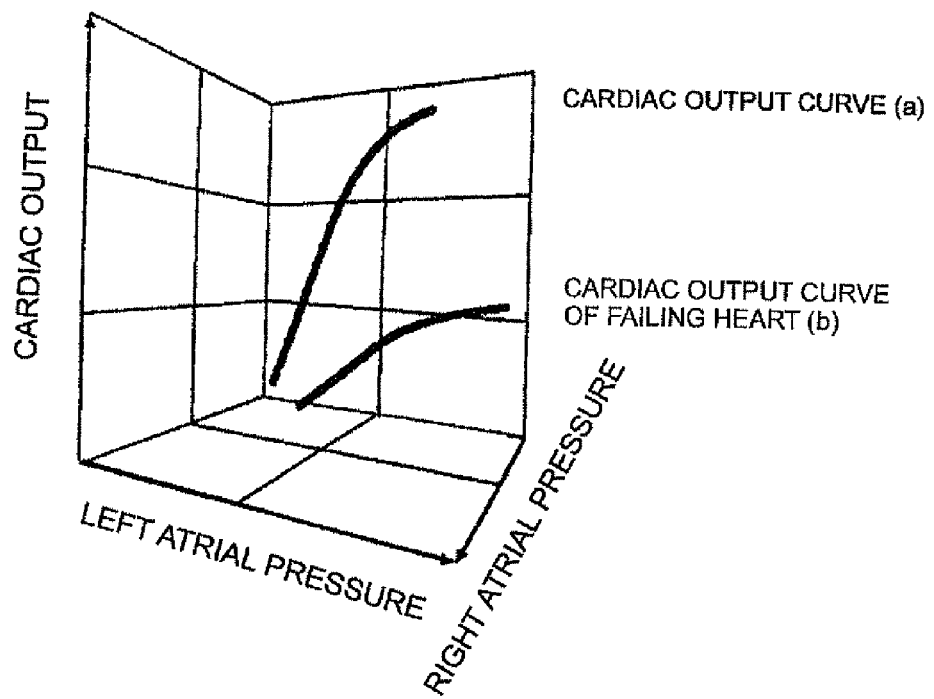

FIG. 3 shows the CO curve of a normal heart (a) and the CO curve of a failing heart (b). Comparing the CO curves (a) and the CO curve (b), it is easy to comprehend that the failing heart has lower integrated cardiac pumping capability of the left and right heart. Presentation of the measured CO curve and a normal CO curve in the same space facilitates diagnosis.

Calculation Means (3) comprises Second Calculation Means (32).

Second Calculation Means (32) calculates effective circulating blood volume from the CO, Pla, and Pra values.

Regarding the method of calculating effective circulating blood volume by Second Calculation Means (32), the CO, Pla value, and Pra values input from Input Means (2) are substituted into Equation 17 as shown below to compute the effective circulating blood volume value.

Constants E, F and G in Equation 17 are constants that can be varied appropriately according to individual patient. These constants are predetermined by the user and can be varied according to patient. Thus adjustment in individual patient allows correction of the calculated effective circulating blood volume value.

$$(CO\ \text{value}) = \frac{1}{E}(\text{effective circulating blood volume value}) - F(Pra\ \text{value}) - G(Pla\ \text{value}) \quad \text{Equation 17}$$

(where E, F, and G are constants)

In using the above Equation 17, it is preferable to convert the equation to Equation 18 as shown below, and to configure such that the effective circulating blood volume is calculated from the input data from Input Means (2). Use of the converted equation allows fast arithmetic processing.

$$(\text{effective circulating blood volume}) = \{(CO)+F(Pra)+G(Pla)\} \times E \quad \text{Equation 18}$$

(where E, F, and G are constants)

Figure 4:
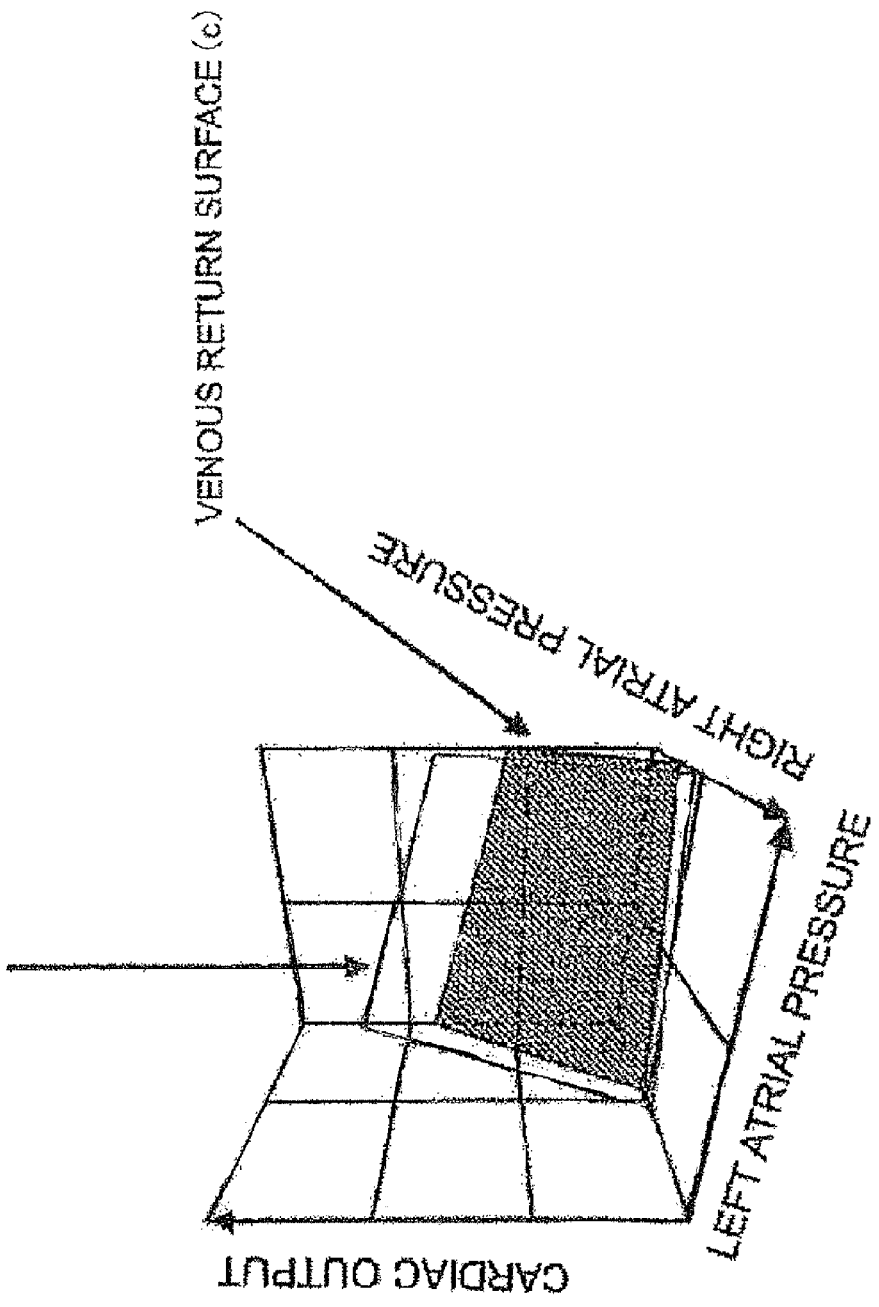

Second Calculation Means (32) calculates using the CO, Pra, and Pla values, and it is possible to show their relationship by plotting "CO" values, "Pra" values, and "Pla" values on three axes of a three dimensional coordinate. In this case, since the "CO" values, "Pla" values, and "Pra" values are treated as three variables, a plane (venous return surface) is formed inside the three-dimensional ordinate as shown in FIG. 4.

The venous return surface is formed by three variables "CO", "Pla", and "Pra" and three constants E, F, and G. It is known that the slope of the surface may be considered constant either between subjects or within subject. It is also possible to correct the slope for a group of patients by their attributes.

Because the slope of the surface is constant, the height of the venous return surface is determined by the calculated effective circulating blood volume.

Therefore, by plotting "CO" values, "Pla" values, and "Pra" values on the three axes of a three dimensional coordinate, the effective circulating blood volume can be represented by the venous return surface. This plot allows visualization of the patient's effective circulating blood volume (venous return surface), which greatly facilitates diagnosis.

FIG. 4 shows the venous return surface under normal condition (c) and the venous return surface of increased effective circulating blood volume (d). Compared to (c), the venous return surface (d) is shifted in parallel with a greater height. Presentation of the normal venous surface and measured venous surface in the same space facilitates diagnosis.

Calculation Means (3) comprises Third Calculation Means (33).

Third Calculation Means (33) calculates vascular resistance from the CO, Pra, and AP values.

Regarding the method of calculating vascular resistance by Third Calculation Means (33), the CO, Pra, and AP values input from Input Means (2) are substituted into Equation 19 as shown below to compute the vascular resistance value.

Constant H in Equation 19 is a constant that corrects the non-linearity of vascular resistance. Thus by adjusting this constant, the system can be operated normally even in individuals showing strong nonlinearity.

$$(\text{vascular resistance}) = \{(AP)-(Pra)-H\}/CO \quad \text{Equation 19}$$

(where H is a constant)

Figure 5:
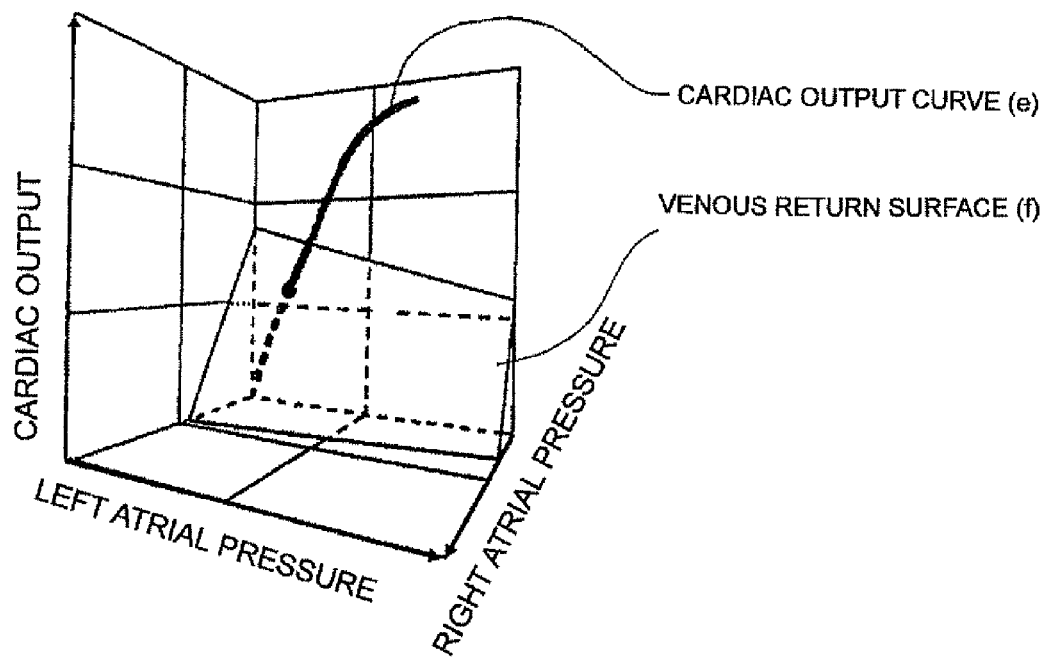

FIG. 5 shows one embodiment of simultaneous presentation of CO curve (e) and venous return surface (f) in a three dimensional coordinate diagram with "CO" values, "Pla" values, and "Pra" values plotted on three axes.

In FIG. 5, the intersection point of CO curve (e) with venous return surface (f) determines the CO value, Pla value, and Pra value of the subject.

If the CO, Pla, and Pra values of an individual are abnormal and require improvement to a certain target values, a target point corresponding to the target values is provided in the three dimensional coordinate diagram. Then the corresponding drugs are administered to control the individual's CO curve (e); i.e. left/right cardiac pumping capability, and venous return surface (f); i.e. effective circulating blood volume, until the intersection of the CO curve (e) with the venous return surface (f) coincides with the target point. By this means, the "CO" value, "Pla" value, and "Pra" value eventually attain the target_normal values.

Comparison Means (4) compares the values calculated in Calculation Means (3) with the target values [target cardiac pumping capability (target left cardiac pumping capability and target right cardiac pumping capability) values, target effective circulating blood volume value, and target vascular resistance value] calculated in Target Decision Means (7). Comparison Means (4) is composed of First Comparison Means (41), Second Comparison Means (42), and Third Comparison Means (43).

First Comparison Means (41) compares the left cardiac pumping capability and right cardiac pumping capability values calculated by First Calculation Means (31) with the target left cardiac pumping capability and target right cardiac pumping capability values calculated in First Target Decision Means (71). More specifically, after First Calculation Means

(31) calculates the left cardiac pumping capability value, First Comparison Means (41) compares the calculated left cardiac pumping capability value with the target left cardiac pumping capability value calculated in First Target Decision Means (71), and depending on the result of comparison, a signals indicating the result of comparison may be sent to Drug Administration Means (5) to be described below.

Through the comparison in First Comparison Means (41), it is possible to categorize the calculated left cardiac pumping capability as "larger than", "equal to", or "smaller than" the target left cardiac pumping capability. According to the comparison result, First Comparison Means (41) sends a signal indicating one of the three results of comparison to the drug administration means [First Drug Administration Means (51) to be described below]. In addition to comparison by three levels of "greater than", "equal to", and "smaller than", First Comparison Means (41) may also send the drug administration means a signal indicating the quantitative deviation of the calculated left cardiac pumping capability from the target left cardiac pumping capability.

The target left cardiac pumping capability value may be set by the user as a default value, as described above. Although an example of left cardiac pumping capability is described above, the right cardiac pumping capability value can also be set in a similar manner as the left cardiac pumping capability. Since the right cardiac pumping capability and the left cardiac pumping capability show identical changes (behaviors), either of the two can be used.

Second Comparison Means (42) compares the effective circulating blood volume value calculated in Second Calculation Means (32) with the target effective circulating blood volume value calculated in Second Target Decision Means (72). More specifically, after Second Calculation Means (32) calculates the effective circulating blood volume value, Second Comparison Means (42) compares the calculated effective circulating blood volume value with the target effective circulating blood volume value calculated in Second Target Decision Means (72), and then sends a signal indicating the result of comparison to Drug Administration Means (5).

Through the comparison in Second Comparison Means (42), it is possible to categorize the calculated effective circulating blood volume as "larger than", "equal to", or "smaller than" the target effective circulating blood volume value. According to this comparison result, Second Comparison Means (42) sends a signal indicating one of the three results of comparison to Drug Administration Means [Second Drug Administration Means (52) to be described below]. In addition to comparison by the three levels of "larger than", "equal to", or "smaller than", Second Comparison Means (42) may send the drug administration means a signal indicating the quantitative deviation of the calculated effective circulating blood volume value from the target effective circulating blood volume value.

The target effective circulating blood volume value may be set by the user as a default value, as described above.

Third Comparison Means (43) compares the vascular resistance value calculated in Third Calculation Means (33) with the target vascular resistance value calculated in Third Target Decision Means (73). More specifically, after Third Calculation Means (33) calculates the vascular resistance value, Third Comparison Means (43) compares the calculated vascular resistance value with the target vascular resistance value calculated in Third Target Decision Means (73), and then sends a signal indicating the result of comparison to Drug Administration Means (5).

Through the comparison in Third Comparison Means (43) it is possible to categorize the calculated vascular resistance value as "larger than", "equal to", or "smaller than" the target vascular resistance value. According to this comparison result, Third Comparison Means (43) sends a signal indicating one of the three results of comparison to drug administration means [Third Drug Administration Means (53) to be described below]. In addition to comparison by the three levels of "larger than", "equal to", or "smaller than", Third Comparison Means (43) may also send the drug administration means a signal indicating the quantitative deviation of the calculated vascular resistance value from the target vascular resistance value.

The target vascular resistance value may be set by the user as a default value, as described above.

Drug Administration Means (5) receives the result of comparison from Comparison Means (4), and starts and stop drug administration to the patient in response to the comparison result.

Drug Administration Means (5) is composed of First Drug Administration Means (51), Second Drug Administration Means (52), and Third Drug Administration Means (53). First to Third Drug Administration Means (51-53) are all configured to administer drugs to a patient, as described below, and also to control the drug administration (adjust the doses of drugs) in response to the signals of comparison results sent from Comparison Means (4).

Drug Administration Means (5) may be, for example, a multi-port type catheter for simultaneous infusion of multiple drugs, which is connected to multiple automatic infusion pumps. The multi-port catheter is placed in the vein of a patient for intravenous administration of drugs.

First Drug Administration Means (51) administers a predetermined drug into the patient's body according to the signal of comparison result sent from First Comparison Means (41).

Because drug administration by First Drug Administration Means (51) is executed according to the signal of comparison result sent from First Comparison Means (41), drug administration is started in the case that abnormal cardiac pumping capability is detected.

Specifically, in the case when First Drug Administration Means (51) receives a signal "smaller than" (when the calculated left cardiac pumping capability is smaller than the target cardiac pumping capability value) from First Comparison Means (41), this indicates that cardiac pumping capability is in an abnormal state, and First Drug Administration Means (51) will start administering drug to increase cardiac pumping capability. The drugs used in this case are inotropic agents such as dobutamine and dopamine.

In another case when First Drug Administration Means (51) receives a signal "equal to" (when the calculated left cardiac pumping capability is equal to the target cardiac pumping capability value) from First Comparison Means (41), this indicates that cardiac pumping capability is in a normal state, and First Drug Administration means (51) will respond by not increasing the dose, or administering no drug, or stopping drug administration.

In yet another case when First Drug Administration Means (51) receives a signal "larger than" (when the calculated left cardiac pumping capability is larger than the target cardiac pumping capability value) from First Comparison Means (41), this indicates that cardiac pumping capability is in a better state than the target, and First Drug Administration Means (51) will respond by reducing the dose of inotropic agent, or administering no drug, or stopping drug administration.

The doses of drugs administered by First Drug Administration Means (51) are not specified, but a dose optimal for the patient's body is the first prerequisite. It is possible to vary the dose based on the deviation of the calculated cardiac pumping capability value from the target cardiac pumping capability value, which is computed by First Comparison Means (41). Although in the above description, the operation of First Drug Administration Means (51) is controlled by categorizing the calculated cardiac pumping capability versus target cardiac pumping capability into three levels of "larger than", "equal to", and "smaller than", it is also possible to divide the deviation from target cardiac pumping capability into multiple levels (more than three levels) and vary the doses of drugs for each level. Dividing the results of comparison into multiple levels and varying the dose according to each level allow highly precise drug administration.

Second Drug Administration Means (52) administers a predetermined drug into the patient's body according to the signal of the comparison result sent from Second Comparison Means (42).

Because drug administration by Second Drug Administration Means (52) is executed according to the signal of comparison sent from Second Comparison Means (42), drug administration is started in the case that abnormal effective circulating blood volume is detected.

Specifically, in the case when Second Drug Administration means (52) receives a signal "larger than" (when the calculated effective circulating blood volume value is larger than the target effective circulating blood volume value) from Second Comparison Means (42), this indicates that the effective circulating blood volume is in an abnormal state, and Second Drug Administration Means (52) will start drug administration to reduce the effective circulating blood volume. The drugs used in this case are diuretics such as furosemide.

In another case when Second Drug Administration Means (52) receives a signal "equal to" (when the calculated effective circulating blood volume value is equal to the target effective circulating blood volume value) from Second Comparison Means (42), this indicates that the effective circulating blood volume is in a normal state, and Second Drug Administration Means (52) will respond by administering no drug or stopping drug administration.

In yet another case when Second Drug Administration Means (52) receives a signal "smaller than" (when the calculated effective circulating blood volume value is smaller than the target effective circulating blood volume value) from Second Comparison Means (42), this indicates that the effective circulating blood volume is in an abnormal state, and second Drug Administration means (52) will start drug administration to increase the effective circulating blood volume. In this case, infusion preparations for increasing effective circulating blood volume, such as low molecular dextran and albumin preparations are used.

As described for First Drug Administration Means (51), the doses of the drugs administered by Second Drug Administration Means (52) are not specified, but a dose optimal for the patient's body is the first prerequisite. It is possible to vary the dose based on the deviation of the calculated effective circulating blood volume from the target effective circulating blood volume, which is computed by Second Comparison Means (42). Dividing the results of comparison of calculated effective circulating blood volume versus target effective circulating blood volume into multiple levels and varying the doses for each level allow highly precise drug administration.

Third Drug Administration Means (53) administers a predetermined drug into the patient's body according to the signal of the comparison result sent from Third Comparison Means (43).

Because drug administration by Third Drug Administration Means (53) is executed according to the signal of comparison sent from Third Comparison Means (43), drug administration is started in the case that abnormal vascular resistance is detected.

Specifically, in the case when Third Drug Administration Means (53) receives a signal "larger than" (when the calculated vascular resistance value is larger than the target vascular resistance value) from Third Comparison Means (43), this indicates that vascular resistance is in an abnormal state, and Third Drug Administration Means (53) will start drug administration to reduce vascular resistance. The drugs used in this case are vasodilators such as nitroprusside, nitroglycerin, and phentolamine. If vasoconstrictors such as norepinephrine are already being administered, the doses of the vasoconstrictors will be reduced.

In another case when Third Drug Administration Means (53) receives a signal "equal to" (when the calculated vascular resistance value is equal to the target vascular resistance value) from Third Comparison Means (43), this indicates that vascular resistance is in a normal state, and Third Drug Administration Means (53) will respond by administering no drug or stopping drug administration.

In yet another case when Third Drug Administration Means (53) receives a signal "smaller than" (when the calculated vascular resistance value is smaller than the target vascular resistance value) from Third Comparison Means (43), this indicates that the vascular resistance is in an abnormal state, and Third Drug Administration Means (53) will start drug administration to increase vascular resistance. The drugs used in this case are vasoconstrictors such as norepinephrine. If vasodilators such as nitroprusside, nitroglycerin, and phentolamine are already being administered, the doses of the vasodilators will be reduced.

As described for First Drug Administration Means (51), the doses of drugs administered by Third Drug Administration Means (53) are not specified, but a dose optimal for the patient's body is the first prerequisite. It is possible to vary the dose based on the deviation of the calculated vascular resistance value from the target vascular resistance value, which is computed by Third Comparison Means (43). Dividing the results of comparison of calculated vascular resistance versus target vascular resistance into multiple levels and varying the dose for each level allow highly precise drug administration.

To adjust the doses of drugs delivered by First to Third Drug Administration Means (51-53), one method is to regulate the doses of drugs at real time to control the real-time cardiac pumping capability, effective circulating blood volume, and vascular resistance in order to attain the target values (target cardiac pumping capability, target effective circulating blood volume, and target vascular resistance) set in First to Third Comparison Means (41-43). In this case, although the control law is not specified, adoption of PI control (proportional integral control) or PID control (proportional integral derivative control) allows optimal dose regulation.

Regulation of the drug doses by PI control or PID control allows highly precise drug administration.

In patients who manifest an idiosyncratic response to drugs, use of adaptive control will allow optimal adjustment of drug doses.

Display Means (6) is an output device that displays the input values (CO, Pla, Pra, and AP) input from Input Means (2) and the calculated values obtained at First to Third Calculation Means (31-33).

Display Means (6) displays the calculated values (cardiac pumping capability, effective circulating blood volume, and vascular resistance) calculated in the respective Calculation Means (31-33). It is preferable to display the data in a continuous time-series line plot because Cardiac Disease Treatment System (1) relating to the present invention has the capability to continuously measure and generate input data from a patient, as described above, and can continuously calculate values in each of the Calculation Means (31-33).

Display of data by time-series of continuous line curves allows visualization and confirmation of chronological changes, facilitating the detection of changes.

Display Means (6) is preferably configured to display the doses of drugs administered by First to Third Drug Administration Means (51-53) because Display Means (6) with additional display of the doses allows the user to observe the changes (transition) in cardiac pumping capability, effective circulating blood volume, and vascular resistance of a patient simultaneously with the doses of drugs administered.

The components of Cardiac Disease Treatment System (1) relating to the present invention have been described thus far.

The operation of Cardiac Disease Treatment System (1) relating to the present invention will be described below.

Figure 6:
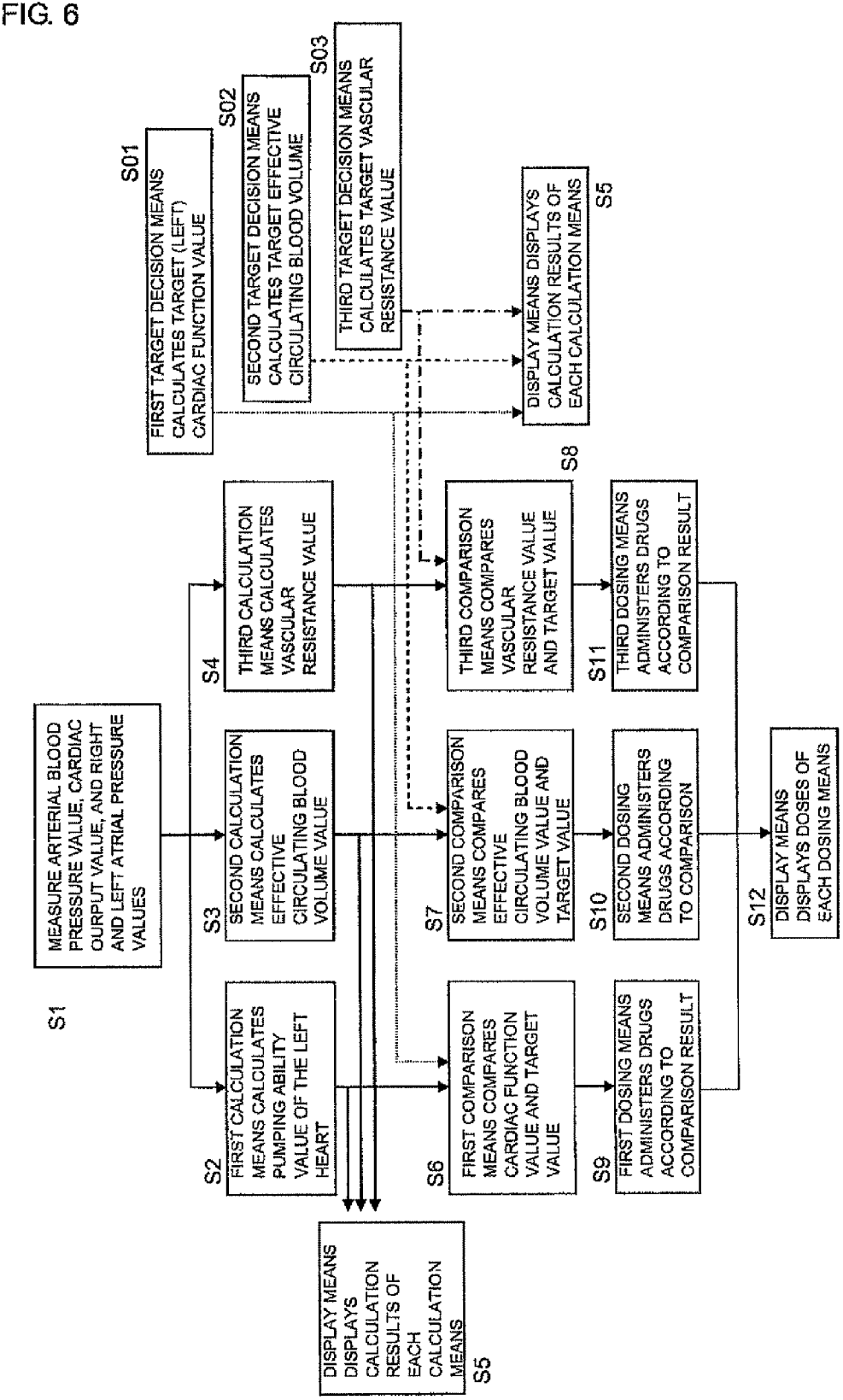
FIG. 6 is a flowchart illustrating use of the cardiac treating system relating to the present invention.

FIG. 6 is a flow chart illustrating the use of the cardiac disease treatment system relating to the present invention.

Although predetermining Constants A to G is required when actually using Cardiac Disease Treatment System (1), the description is omitted here. The target CO, target Pra, target Pla, and target AP values set in Target Decision Means (7) [First to Third Target Decision Means (71-73)] are predetermined values to be decided by the user.

First, the user decides target CO, target Pra, target Pla, and target AP values that represent the desired conditions of the patient, and input them into Target Decision Means (7).

From the target CO, target Pra, target Pla, and target AP values input by the user, Target Decision Means (7) calculates the target left cardiac pumping capability, target right cardiac pumping capability, target effective circulating blood volume, and target vascular resistance values.

Specifically, after the target CO and target Pla values are input into First Decision Means (71), target left cardiac pumping capability value is calculated. In addition, after the target CO and target Pra values are input into First target Decision Means (71), target right cardiac pumping capability value (S01) is calculated.

After the target CO, target Pla value, and target Pra values are input into Second Target Decision Means (72), the target effective circulating blood volume value (S02) is calculated.

After the target CO, target Pra, and target AP values are input into Third Target Decision Means (73), the target vascular resistance value (S03) is calculated.

After the target values (target left cardiac pumping capability, target right cardiac pumping capability, target effective circulating blood volume, and target vascular resistance) are calculated by Target Decision Means (7), these target values are sent to Display Means (6). The target values sent to Display Means (6) are displayed in continuous time-series line curves (see S5 to be described below).

Next, the patient's AP, CO, Pra, and Pla are measured (S1).

These values may be measured by inserting a Swan-Ganz catheter into the patient, although other devices may also be used.

The measured AP, CO, Pra, and Pla values are input from Input Means (2) into Calculation Means (3).

After these measured values are input from Input Means (2), Calculation Means (3) calculates the left cardiac pumping capability, right cardiac pumping capability, effective circulating blood volume, and vascular resistance values. Specifically, after the CO and Pla values are input into First Calculation Means (31), left cardiac pumping capability value is calculated. In addition, after CO and Pra values are input into First Calculation Means (31), right cardiac pumping capability value (S2) is calculated.

After the CO, Pla, and Pra values are input into Second Calculation Means (32), the effective circulating blood volume value (S3) is calculated.

After the CO, Pra, and AP values are input into Third Calculation Means (33), the vascular resistance value (S4) is calculated.

From the CO, Pla, Pra, and AP values generated from each measurement, First to Third Calculation Means (31-33) respectively calculate the left cardiac pumping capability, right cardiac pumping capability, effective circulating blood volume, and vascular resistance, in a continuous manner.

After all the values (left cardiac pumping capability, right cardiac pumping capability, effective circulating blood volume, and vascular resistance) are calculated by Calculation Means (3), these calculated values are sent to Display Means (6). The calculated values sent to Display Means (6) are displayed in continuous time-series line curves (S5).

Next, because the left cardiac pumping capability value calculated in First Calculation Means (31) is sent to First Comparison Means (41) while the target left cardiac pumping capability value calculated in First Target Decision Means (71) is also sent to First Comparison Means (41), First Comparison Means (41) compares the left (or right) cardiac pumping capability value with the target left (or right) cardiac pumping capability value (S6).

First Comparison Means (41) sends the result of comparison between the calculated left cardiac pumping capability value and target left cardiac pumping capability value to First Drug Administration Means (51).

Because the effective circulating blood volume value calculated in Second Calculation Means (32) is sent to Second Comparison Means (42) while the target effective circulating blood volume value calculated in Second Target Decision Means (72) is also sent to Second Comparison Means (42), Second Comparison Means (42) compares the effective circulating blood volume value with the target effective circulating blood volume value (S7).

Second Comparison Means (42) sends the result of comparison between the calculated effective circulating blood volume value and target effective circulating blood volume value to Second Drug Administration Means (52).

Because the vascular resistance value calculated in Third Calculation Means (33) is sent to Third Comparison Means (43) while the target vascular resistance value calculated in Third Target Decision Means (73) is also sent to Third Comparison Means (43), Third Comparison Means (43) compares the vascular resistance value with the target vascular resistance value (S8).

Third Comparison Means (43) sends the result of comparison between the calculated vascular resistance value and target vascular resistance value to Third Drug Administration Means (53).

First Drug Administration Means (51) receives the comparison result obtained in First Comparison Means (41) and then administers drug according to this comparison result (S9).

If the comparison result from First Comparison Means (41) prompts drug administration by First Drug Administration Means (51) (in the case that the calculated cardiac pumping capability value is smaller than the target cardiac pumping capability value), First Drug Administration Means (51) administers inotropic agent to the patient to increase the patient's cardiac pumping capability.

If the comparison result indicates stopping of drug administration or no need for drug administration by First Drug Administration Means (51) (in the case that the calculated cardiac pumping capability value is equal to the target cardiac pumping capability value), First Drug Administration Means (51) stops drug administration or maintains a stopping state.

If the comparison result indicates no need for inotropic agent administration by First Drug Administration Means (51) (in the case that the calculated cardiac pumping capability value is larger than the target cardiac pumping capability value), First Drug Administration Means (51) reduces the dose of inotropic agent, or stops drug administration, or maintains a stopping state.

Second Drug Administration Means (52) receives the comparison result obtained in Second Comparison Means (42) and then administers drugs according to this comparison result (S10).

If the comparison result from Second Comparison Means (42) prompts drug administration by Second Drug Administration means (52) (in the case that the calculated effective circulating blood volume value is smaller than the target effective circulating blood volume value), Second Drug Administration Means (52) administers appropriate infusion preparation (low molecular dextran or albumin preparation) to the patient to increase the patient's effective circulating blood volume.

If the comparison result indicates stopping of drug administration or no need for drug administration by Second Drug Administration Means (52) (in the case that the calculated effective circulating blood volume value is equal to the target effective circulating blood volume value), Second Drug Administration Means (52) stops drug administration or maintains a stopping state.

If the comparison result prompts drug administration by Second Drug Administration Means (52) (in the case that the calculated effective circulating blood volume value is larger than the target effective circulating blood volume value), Second Drug Administration Means (52) administers diuretics to the patient to reduce the patient's effective circulating blood volume.

Third Drug Administration Means (53) receives the comparison result obtained in Third Comparison Means (43) and then administers drugs according to this comparison result (S11).

If the comparison result from Third Comparison Means (43) prompts drug administration by Third Drug Administration Means (53) (in the case that the calculated vascular resistance value is smaller than the target vascular resistance value), Third Drug Administration Means (53) administers vasoconstrictor to the patient to increase the patient's vascular resistance.

If the comparison result indicates stopping of drug administration or no need for drug administration by Third Drug Administration Means (53) (in the case that the calculated vascular resistance value is equal to the target vascular resistance value), Third Drug Administration Means (53) stops drug administration or maintains a stopping state.

If the comparison result prompts drug administration by Third Drug Administration Means (53) (in the case that the calculated vascular resistance value is larger than the target vascular resistance value), Third Drug Administration Means (53) administers vasodilator to the patient to reduce the patient's vascular resistance.

As described above, First to Third Drug Administration Means (51-53) may administer drugs with doses adjusted for multiple levels, or regulate the doses by control methods (such as PI control and PID control) that determine the doses at real time. In patients who manifest an idiosyncratic response to drugs, the doses may be regulated by an adaptive control.

Display Means (6) displays the time sequences of cardiac pumping capability (left cardiac pumping capability and right cardiac pumping capability), effective circulating blood volume, and vascular resistance values calculated by First to Third Calculation Means (31-33); the target cardiac pumping capability (target left cardiac pumping capability and target right cardiac pumping capability), target effective circulating blood volume, and target vascular resistance values calculated by First to Third Target Decision Means (71-73); and the doses of drugs administered in response to these calculated values (S12).

By displaying said calculated values, target values, and doses on Display Means (6), the user of Cardiac Disease Treatment System (1) is able to diagnose the patient's conditions chronologically.

Example 1

The results of an experiment on Cardiac Disease Treatment System (I) relating to the present invention will be shown below.

In this experimental example, the accuracy of the equations (Equations 13 to Equation 18) used in Cardiac Disease Treatment System (1) relating to the present invention was tested.

Seven dogs were used to examine the validity of these equations.

First, Constants A and B in Equations 13 and 14 are examined. These constants are employed in calculating the left cardiac pumping capability of the dogs.

As shown in Table 1 below, in dogs, Constants A and B are determined as "A=2.03" and "B=0.80".

TABLE 1

| Dog | Left cardiac pumping capability | A | B | Determination coefficient | Standard error of estimate |
|---|---|---|---|---|---|
| 1 | 58.1 | 1.27 | 0.61 | 0.98 | 4.3 |
| 2 | 24.4 | 2.03 | 2.71 | 0.95 | 3.6 |
| 3 | 108.4 | 0.00 | −0.67 | 0.95 | 5.6 |
| 4 | 66.7 | 2.08 | 0.08 | 0.98 | 5.9 |
| 5 | 105.6 | 2.30 | −0.02 | 0.99 | 5.0 |
| 6 | 73.5 | 2.21 | 0.59 | 0.99 | 2.5 |
| 7 | 42.0 | 4.32 | 2.30 | 0.98 | 4.7 |
| Mean | 68.4 | 2.03 | 0.80 | 0.97 | 4.5 |
| Standard Deviation | 30.9 | 1.29 | 1.25 | | 1.2 |

Next, Constants C and D in Equations 15 and 16 are examined. These constants are employed in calculating the right cardiac pumping capability of the dogs.

As shown in Table 2 below, in dogs, Constants C and D are determined as "C=1.0" and "D=0.88".

"Constant C" and "Constant D" are obtained by performing linear regression on the above seven measured values, with adjustment for practical use.

TABLE 2

| Dog | Right cardiac pumping capability | C | D | Determination coefficient | Standard error of estimate |
|---|---|---|---|---|---|
| 1 | 46.7 | 2.12 | 2.34 | 0.98 | 4.7 |
| 2 | 33.9 | 1.50 | 2.50 | 0.96 | 3.3 |
| 3 | 64.1 | 2.10 | 2.10 | 0.90 | 8.2 |

TABLE 2-continued

| Dog | Right cardiac pumping capability | C | D | Determination coefficient | Standard error of estimate |
|---|---|---|---|---|---|
| 4 | 112.7 | 1.39 | 0.19 | 0.98 | 5.5 |
| 5 | 101.8 | 1.39 | 0.92 | 0.99 | 4.6 |
| 6 | 80.6 | 3.07 | 1.59 | 0.99 | 2.8 |
| 7 | 37.1 | 3.33 | 3.69 | 0.94 | 6.8 |
| Mean | 68.1 | 2.13 | 1.90 | 0.96 | 5.1 |
| Standard Deviation | 31.3 | 0.80 | 1.14 | | 1.9 |

Next, Constants E, F, and G in Equations 17 and 18 are examined. These constants are employed in calculating the effective circulating blood volume of the dogs.

As shown in Table 3 below, in dogs, Constants E, F, and G are determined as "E=0.129", "F=19.61", and "G=3.49".

TABLE 3

| Dog | E | F | G | Determination coefficient | Standard error of estimate |
|---|---|---|---|---|---|
| 1 | 0.154 | 19.77 | 3.83 | 0.99 | 1.9 |
| 2 | 0.232 | 23.30 | 3.39 | 0.92 | 7.4 |
| 3 | 0.099 | 20.99 | 4.04 | 0.97 | 3.7 |
| 4 | 0.088 | 17.60 | 2.92 | 0.99 | 1.3 |
| 5 | 0.092 | 16.17 | 3.46 | 0.92 | 6.5 |
| 6 | 0.107 | 19.01 | 4.26 | 0.99 | 1.5 |
| 7 | 0.132 | 20.44 | 2.55 | 0.99 | 1.2 |
| Mean | 0.129 | 19.61 | 3.49 | 0.97 | 3.4 |
| Standard Deviation | 0.051 | 2.33 | 0.61 | | 2.6 |

By the above procedures, the default values of Constants A to G are determined. In other words, if the subjects (patients) are dogs, Constants A to G in Equations 13 to 18 are determined as "A=2.03", "B=0.80", "C=1.0", "D=0.88", "E=0.129", "F=19.61", and "G=3.49". Constant H in Equation 19 is determined as "H=0" for dogs, according to the study by Shoukas et. al. (see Shoukas AA. Carotid sinus baroreceptor reflex control and epinephrine. Influence on capacitive and resistive properties of the total pulmonary vascular bed of the dog. Circ Res 51:95-101, 1982).

Cardiac Disease Treatment System (1) is operated with the use of these constants.

Figure 7:
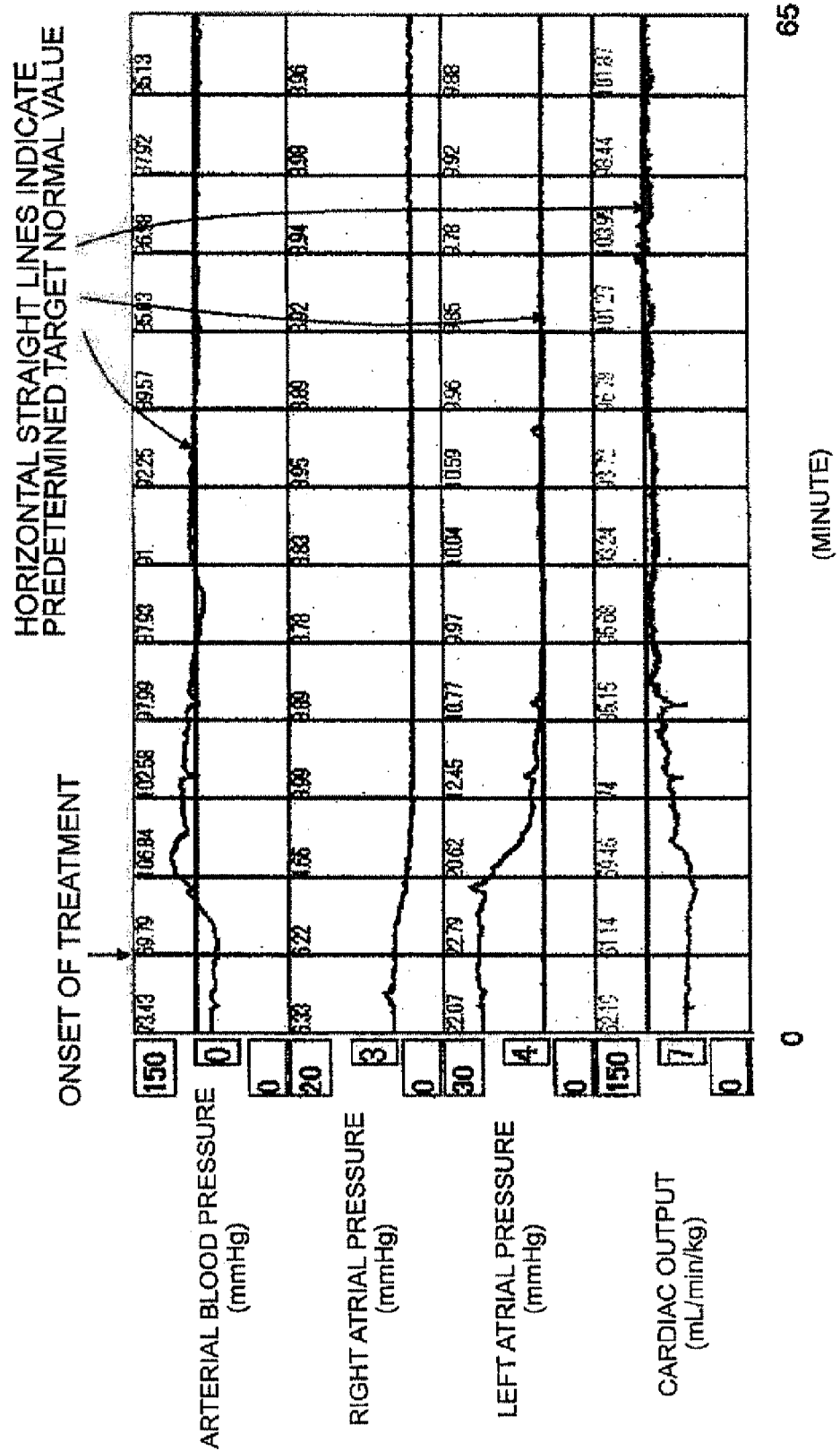
FIG. 7 shows changes in arterial blood pressure, right atrial pressure, left atrial pressure, and cardiac output value during use of the cardiac disease treatment system relating to the present invention.
Figure 8:
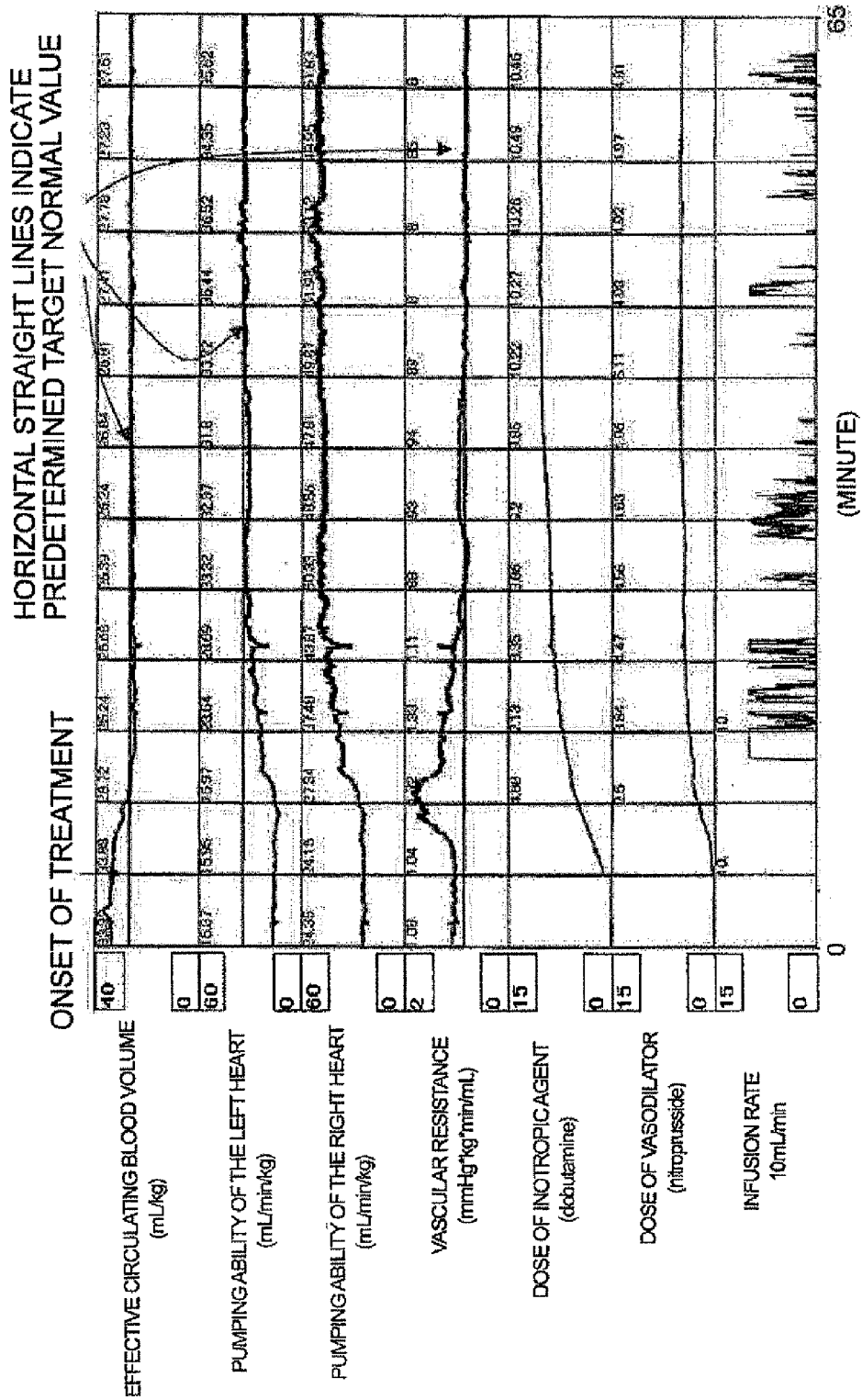
FIG. 8 shows changes in effective circulating blood volume, left cardiac pumping capability, right cardiac pumping capability, vascular resistance, and changes in drug doses during use of the cardiac disease treatment system relating to the present invention. The horizontal line in each trace displays the target left cardiac pumping capability, target effective circulating blood volume, or target vascular resistance.

FIGS. 7 and 8 show one example of the use of the cardiac disease treatment system relating to the present invention.

FIG. 7 shows the chronological changes in AP, Pra, Pla, and CO. As shown in FIG. 7, AP, Pra, Pla, and CO attain target values within 20 minutes from the start of treatment. The target values in this example were set as "AP=90 mmHg", "Pla=10 mmHg", and "CO=100 ml/min/kg".

FIG. 8 shows the chronological changes in effective circulating blood volume, left cardiac pumping capability, right cardiac pumping capability, vascular resistance, doses of inotropic agent and vasodilator, and infusion volume. Dobutamine is used as inotropic agent, nitroprusside as vasodilator; and low molecular dextran as intravenous infusion. PI control is used in determining the doses of inotropic agent and vasodilator, while multi-level control is used in determining the infusion volume.

As shown in FIG. 8, at the start of treatment, the effective circulating blood volume is higher than the target effective circulating blood volume; the left cardiac pumping capability and right cardiac pumping capability are lower than the target left cardiac pumping capability and target right cardiac pumping capability; and the vascular resistance is higher than the target vascular resistance. All these parameters are in abnormal states deviated from the target values [Effective circulating blood volume, left cardiac pumping capability, right cardiac pumping capability, and vascular resistance values are calculated by Calculation Means (3), and the states of these parameters (whether in a normal or abnormal state) are determined by Comparison Means (4)].

When treatment is started, Drug Administration Means (5) starts administering drugs in response to the corresponding states in an attempt to bring the calculated values toward the target values [Drug Administration Means (5) administers optimal doses of drugs]. The above process is repeated until the calculated values attain the respective target values.

As described above, by using Cardiac Disease Treatment System (1) relating to the present invention, it is possible to control the patient's cardiac pumping capability, effective circulating blood volume, and vascular resistance values to desired values, and thereby controlling the CO, Pla, and AP values to target values.

What is claimed is:

1. A cardiac disease treatment system comprising:
   an input means inputting a cardiac output value, a left atrial pressure value, and/or a right atrial pressure value of a patient;
   a first calculation means calculating a pumping ability value of the left heart or a pumping ability value of the right heart from the cardiac output value, the left atrial pressure value, and the right atrial pressure value which are input from the input means;
   a first comparison means comparing calculated values of the pumping ability value of the left heart and/or the pumping ability value of the right heart and target pumping ability values; and
   a first dosing means administering drugs to the patient according to comparison results in the first comparison means.

2. The cardiac disease treatment system according to claim 1, wherein the first calculation means uses equation 1 and/or equation 2 to calculate the pumping ability value of the left heart and/or the pumping ability value of the right heart from the cardiac output value, the left atrial pressure value, and/or the right atrial pressure value input by the input means;

$$\text{(cardiac output)} = \text{(left cardiac pumping capability)} \times \{\text{Log}((\text{left atrial pressure})A) + B\} \quad \text{Equation 1}$$

where A and B are constants;

$$\text{(cardiac output)} = \text{(right cardiac pumping capability)} \times \{\text{Log}((\text{right atrial pressure})C) + D\} \quad \text{Equation 2}$$

where C and D are constants.

3. The cardiac disease treatment system according to claim 1, further comprising:
   a first target decision means calculating a target pumping ability value of the left heart and/or a target pumping ability value of the right heart as the target pumping ability value from the target cardiac output value, the target left atrial pressure value, and/or the target right atrial pressure value.

4. The cardiac disease treatment system according to claim 3, wherein the first target decision means uses equation 3 and equation 4 to calculate the target pumping ability value of the left heart and/or the pumping ability value of the right heart from the target cardiac output value, the target left atrial pressure value, and/or the right atrial pressure value:

$$\text{(target left cardiac pumping capability)} = \text{(target cardiac output)} / \{\text{Log}((\text{target left atrial pressure})A) + B\} \quad \text{Equation 3}$$

where A and B are constants;

$$\text{(target right cardiac pumping capability)} = \text{(target cardiac output value)}/\{\text{Log}((\text{target right atrial pressure})C)+D\} \quad \text{Equation 4}$$

where C and D are constants.

5. The cardiac disease treatment system according to claim 1, further comprising:
   a display means continuously displaying each of the calculated values calculated by the calculation means in chronological order.

6. The cardiac disease treatment system according to claim 1, wherein the cardiac output value is measured by a Swan-Ganz catheter or calculated from a diastolic time constant of arterial blood pressure waveform.

7. The cardiac disease treatment system according to claim 1, wherein the left atrial pressure value is directly measured by a catheter or continuously estimated from diastolic pressure values of pulmonary capillary wedge pressure or pulmonary arterial pressure which are measured by a Swan-Ganz catheter.

8. A cardiac disease treatment system comprising:
   an input means inputting a cardiac output value, a left atrial pressure value, and a right atrial pressure value of a patient;
   a second calculation means calculating an effective circulating blood volume value from the cardiac output value, the left atrial pressure value, and the right atrial pressure value which are input from the input means;
   a second comparison means comparing the effective circulating blood volume value calculated by the second calculation means and a target effective circulating blood volume value; and
   a second dosing means administering drugs to the patient according to the comparison result in the second comparison means.

9. The cardiac disease treatment system according to claim 8 wherein the second comparison means uses equation 5 to calculate the effective circulating blood volume value from the cardiac output value, the left atrial pressure value, and the right atrial pressure value input by the input means;

$$\text{(cardiac output)} = \frac{1}{E}\text{(effective circulating blood volume)} - F\text{(right atrial pressure)} - G\text{(left atrial pressure)} \quad \text{Equation 5}$$

where E, F, and G are constants.

10. The cardiac disease treatment system according to claim 8, further comprising:
    a second target decision means calculating a target effective circulating blood volume value from the target cardiac output value, the target left atrial pressure value, and the target right atrial pressure value.

11. The cardiac disease treatment system according to claim 10, wherein the second target decision means uses equation 6 to calculate the target effective circulating blood volume value from the target cardiac output value, the target left atrial pressure value, and/or the target right atrial pressure value:

$$\text{(target effective circulating blood volume)} = \{\text{(target cardiac output)} + F\text{(target right atrial pressure)} + G\text{(target left atrial pressure)}\} \times E \quad \text{Equation 6}$$

where E, F, and G are constants.

12. The cardiac disease treatment system according to claim 1, further comprising:
    a display means continuously displaying each of the calculated values calculated by the calculation means in chronological order.

13. The cardiac disease treatment system according to claim 8, wherein the cardiac output value is measured by a Swan-Ganz catheter or calculated from a diastolic time constant of arterial blood pressure waveform.

14. The cardiac disease treatment system according to claim 8, wherein the left atrial pressure value is directly measured by a catheter or continuously estimated from diastolic pressure values of pulmonary capillary wedge pressure or pulmonary arterial pressure which are measured by a Swan-Ganz catheter.

15. A cardiac disease treatment system comprising:
    an input means inputting a cardiac output value, a right atrial pressure value, and an arterial blood pressure value of a patient;
    a third calculation means calculating a vascular resistance value from the cardiac output value, the right atrial pressure value, and the arterial blood pressure value which are input by the input means;
    a third comparison means comparing the vascular resistance value calculated by the third calculation means and a target vascular resistance value; and
    a third dosing means administering drugs to the patient according to the comparison result in the third comparison means.

16. The cardiac disease treatment system according to claim 15, wherein the third comparison means uses equation 7 to calculate the vascular resistance value from the cardiac output value, the right atrial pressure value, and the arterial blood pressure value input by the input means:

$$\text{(vascular resistance)} = \{\text{(arterial blood pressure)} - \text{(right atrial pressure)} - H\}/\text{(cardiac output)} \quad \text{Equation 7}$$

where H is a constant.

17. The cardiac disease treatment system according to claim 15, further comprising:
    a third target decision means calculating a target vascular resistance value from the target cardiac output value, the target arterial blood pressure value, and the target right atrial pressure value.

18. The cardiac disease treatment system according to claim 17, wherein the third target decision means uses equation 8 to calculate the target vascular resistance value from the target cardiac output value, the target arterial blood pressure value, and the target right atrial pressure value:

$$\text{(target vascular resistance)} = \{\text{(target arterial blood pressure)} - \text{(target right atrial pressure)} - H\}/\text{(target cardiac output)} \quad \text{Equation 8}$$

where H is a constant.

19. The cardiac disease treatment system according to claim 15, further comprising: a display means continuously displaying each of the calculated values calculated by the calculation means in chronological order.

20. The cardiac disease treatment system according to claim 15, wherein the cardiac output value is measured by a Swan-Ganz catheter or calculated from a diastolic time constant of arterial blood pressure waveform.

21. The cardiac disease treatment system according to claim 15, wherein the left atrial pressure value is directly measured by a catheter or continuously estimated from diastolic pressure values of pulmonary capillary wedge pressure or pulmonary arterial pressure which are measured by a Swan-Ganz catheter.

22. A cardiac disease treatment system that is a combination of two or three of the systems defined in following (i) to (iii), (i) A cardiac disease treatment system comprising:
an input means inputting a cardiac output value, a left atrial pressure value, and/or a right atrial pressure value of a patient;
a first calculation means calculating a pumping ability value of the left heart or a pumping ability value of the right heart from the cardiac output value, the left atrial pressure value, and the right atrial pressure value which are input from the input means;
a first comparison means comparing calculated values of the pumping ability value of the left heart and/or the pumping ability value of the right heart and target pumping ability values; and
a first dosing means administering drugs to the patient according to comparison results in the first comparison means, (ii) A cardiac disease treatment system comprising:
an input means inputting a cardiac output value, a left atrial pressure value, and a right atrial pressure value of a patient;
a second calculation means calculating an effective circulating blood volume value from the cardiac output value, the left atrial pressure value, and the right atrial pressure value which are input from the input means;
a second comparison means comparing the effective circulating blood volume value calculated by the second calculation means and a target effective circulating blood volume value; and
a second dosing means administering drugs to the patient according to the comparison result in the second comparison means, (iii) A cardiac disease treatment system comprising:
an input means inputting a cardiac output value, a right atrial pressure value, and an arterial blood pressure value of a patient;
a third calculation means calculating a vascular resistance value from the cardiac output value, the right atrial pressure value, and the arterial blood pressure value which are input by the input means;
a third comparison means comparing the vascular resistance value calculated by the third calculation means and a target vascular resistance value; and
a third dosing means administering drugs to the patient according to the comparison result in the third comparison means.

23. The cardiac disease treatment system according to claim 22, further comprising:
a display means continuously displaying each of the calculated values calculated by the calculation means in chronological order.

24. The cardiac disease treatment system according to claim 22, wherein the cardiac output value is measured by a Swan-Ganz catheter or calculated from a diastolic time constant of arterial blood pressure waveform.

25. The cardiac disease treatment system according to claim 22, wherein the left atrial pressure value is directly measured by a catheter or continuously estimated from diastolic pressure values of pulmonary capillary wedge pressure or pulmonary arterial pressure which are measured by a Swan-Ganz catheter.

* * * * *